United States Patent

Bird et al.

[11] Patent Number: 5,830,219
[45] Date of Patent: Nov. 3, 1998

[54] APPARATUS FOR HOLDING AND DRIVING A SURGICAL CUTTING DEVICE USING STEREOTACTIC MAMMOGRAPHY GUIDANCE

[75] Inventors: Richard R. Bird, Bethel, Conn.; Kenneth F. DeFrietas, Patterson, N.Y.; Roman R. Janer, Danbury, Conn.; Hal Kirshner, Weston, Conn.; Samson L. Pennatto, Danbury, Conn.

[73] Assignee: Trex Medical Corporation, Danbury, Conn.

[21] Appl. No.: 805,124

[22] Filed: Feb. 24, 1997

[51] Int. Cl.$^6$ ............................. A61B 19/00; A61B 10/00

[52] U.S. Cl. ......................... 606/130; 600/562; 600/568; 600/429

[58] Field of Search ................................. 604/116; 606/1, 606/116, 130; 600/424, 429

[56] References Cited

U.S. PATENT DOCUMENTS

| | | | |
|---|---|---|---|
| 4,875,478 | 10/1989 | Chen | 606/130 |
| 5,415,169 | 5/1995 | Siczek et al. | 606/130 |
| 5,649,936 | 7/1997 | Real | 606/130 |
| 5,695,500 | 12/1997 | Taylor et al. | 606/130 |

*Primary Examiner*—Glenn K. Dawson
*Attorney, Agent, or Firm*—Ware, Fressola, Van Der Sluys & Adolphson LLP

[57] ABSTRACT

An apparatus for holding and driving a rotary cutting surgical instrument with a needle guiding stage of a stereotactic mammography biopsy system is disclosed. The system includes a rotary cutting surgical instrument having a housing with a mechanism for securing the housing to a needle guiding stage of the stereotactic mammography biopsy system. The apparatus further includes a position encoder and controller for determining the resistance experienced by the rotary cutting instrument and for controlling the rotation of the instrument in response to the resistance.

3 Claims, 5 Drawing Sheets

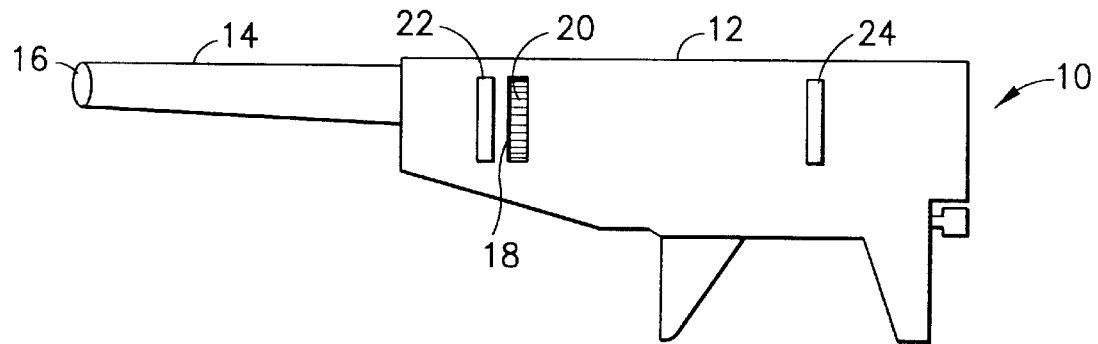
FIG. 2
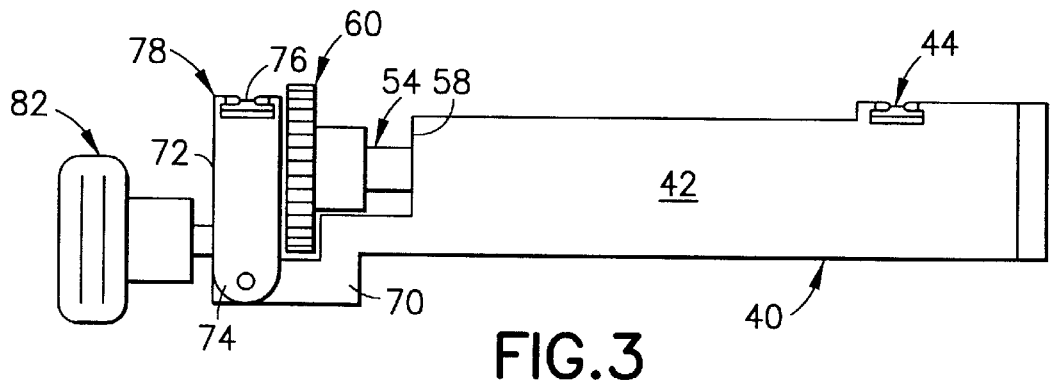
FIG. 3
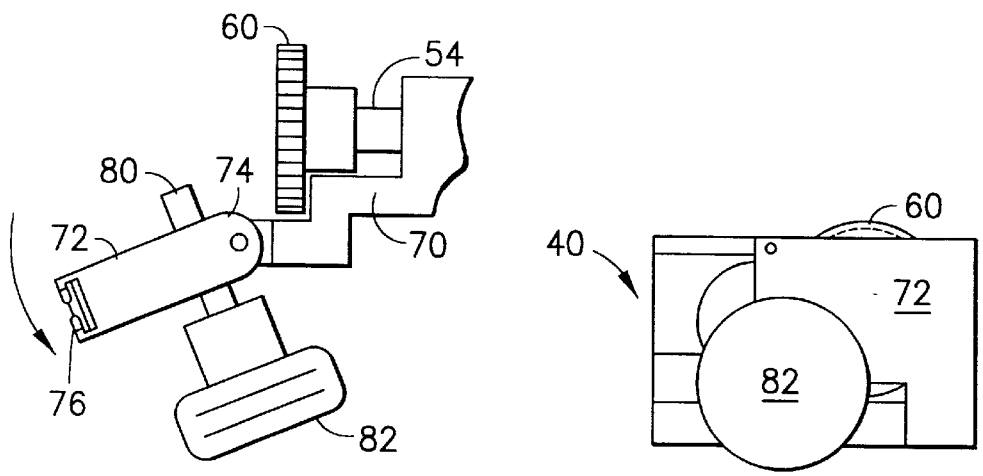
FIG. 4
FIG. 5

APPARATUS FOR HOLDING AND DRIVING A SURGICAL CUTTING DEVICE USING STEREOTACTIC MAMMOGRAPHY GUIDANCE

BACKGROUND OF THE INVENTION

1. Field of the Invention

The present invention generally relates to an apparatus which enables a hand held surgical cutting device to be used with a prone stereotactic mammographic guided needle breast biopsy system so that suspicious lesions may be surgically removed under stereotactic mammography guidance.

2. Description of the Prior Art

Stereotactic mammography is currently used to determine the three-dimensional location of a suspicious lesion in a breast so that the lesion may be sampled to determine whether it is malignant. In a typical stereotactic mammographic biopsy procedure, a patient's breast is stereotactically imaged. The coordinates of the lesion appearing in the stereotactic images are measured and are used to determine the three-dimensional coordinates of a suspicious lesion. A biopsy needle, mounted on a needle guiding stage, is inserted into the breast to obtain a sample of cells or tissue in the suspicious area. The cells or tissue samples are analyzed by a cytologist or pathologist. When analysis of the sample of cells or tissue indicates that the sample may be malignant, surgical excision of tissue in the sampled area is typically recommended and performed.

U.S. Surgical Corporation makes a hand held surgical coring instrument which may be used to surgically excise tissue from an area of interest in a breast. The device comprises a body, a cannula, and a cylindrical cutting tip disposed within the cannula. During an operation, a rack is mounted to the body, and the body is hand held by a surgeon. The rack, connected to a gear in the body which in turn is connected to the cylindrical cutting tip, is moved back and forth in a reciprocating manner to cause the cylindrical cutting tip to rotate in a reciprocating manner. As the cylindrical cutting tip rotates back and forth, a core of tissue is cut and the remaining tissue is cauterized by an associated heating element.

This surgical instrument could be used in conjunction with stereotactic mammographic imaging as a means for guiding the surgical instrument precisely into the affected area of a breast to remove suspicious tissue therefrom. However, it is believed that the precision afforded by stereotactic mammographic imaging can not be fully utilized by this surgical instrument when it is held and driven by hand, as designed. In other words, the placement accuracy and rotational velocity of the cutting tip cannot be controlled well by hand.

SUMMARY OF THE INVENTION

Accordingly, it is a principal object of the present invention to adapt and support a normally hand held rotary cutting surgical instrument, enabling it to be used accurately and conveniently while guided by a stereotactic needle biopsy apparatus for performing accurate, minimally invasive surgical techniques on a breast to remove suspicious tissue.

This object is accomplished, at least in part, by providing an apparatus, which can be held by the needle guiding stage of a stereotactic mammography biopsy system, for holding and driving a rotary cutting surgical instrument with a stereotactic mammography biopsy system. The apparatus comprises a housing having means for securely supporting a rotary cutting surgical instrument and having means for securing the apparatus to a needle guiding stage of a stereotactic mammography system; a motor having a shaft, the motor positioned within the housing; a position encoder within the housing, the position encoder connected to the shaft of the motor; a surgical instrument driving gear connected to the shaft of the motor, the gear being located at a drive end of the housing; a swing arm hingeably attached to the housing at the drive end, the swing arm having means for securing the rotary cutting surgical instrument to the apparatus, the swing arm further including biasing means for adjusting the position of the securing means thereon relative to the securing means on the housing; and a motor controlling means for monitoring and controlling the motion of the motor.

Other objects and advantages of the present invention will become apparent to those skilled in the art from the following detailed description read in conjunction with the attached drawings and claims appended hereto.

BRIEF DESCRIPTION OF THE DRAWINGS

The drawings, not drawn to scale, include:

FIG. 2 is a side view of the hand held rotary cutting surgical instrument;

FIG. 3 is a side view of the apparatus of the present invention;

FIG. 4 is a view of the gear end of the apparatus of the present invention illustrating the swing arm in a lowered position;

FIGS. 5 is a side view of the gear end of the apparatus with the swing arm in an upward position as illustrated in FIG. 3;

BEST MODE FOR CARRYING OUT THE INVENTION

Figure 1:
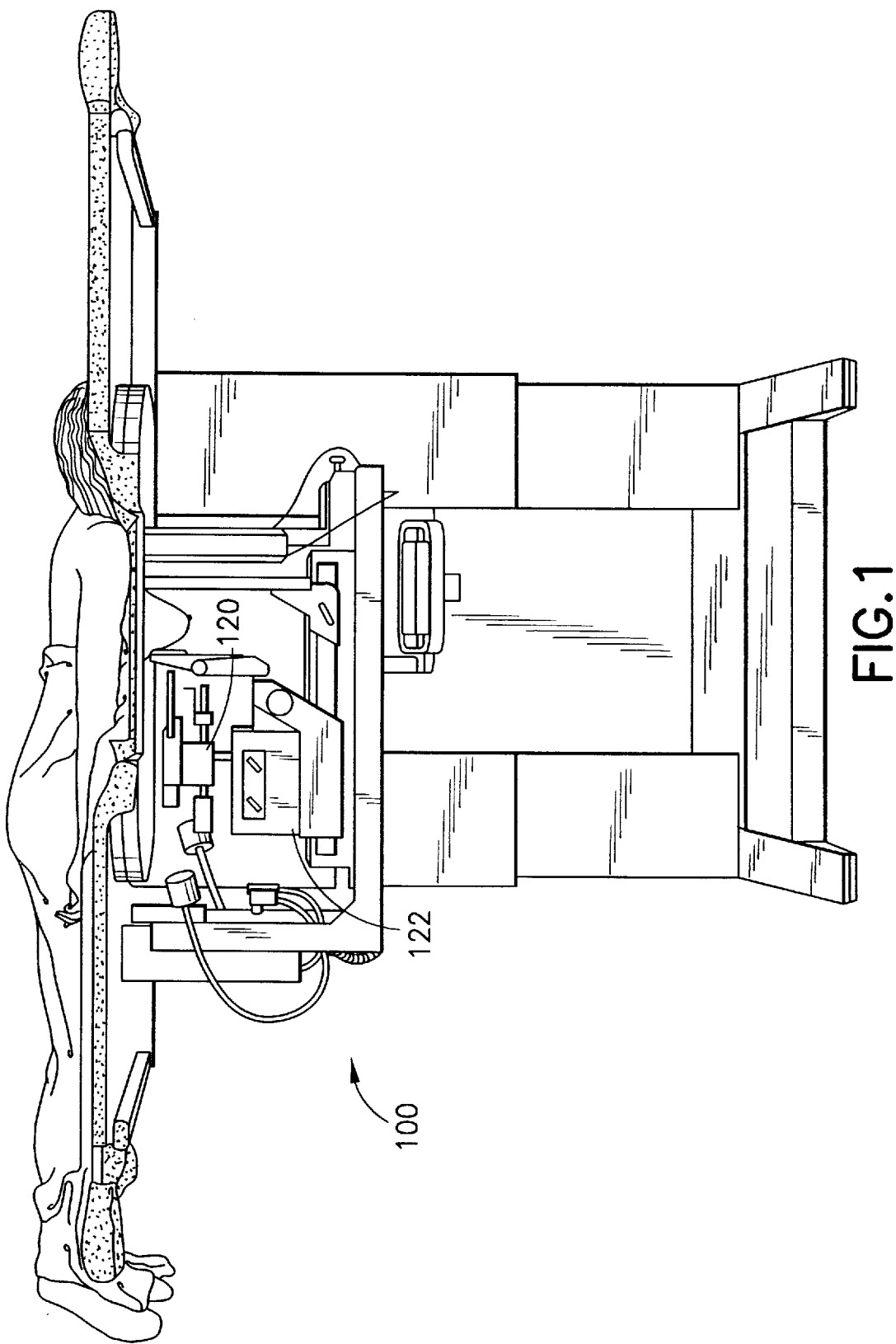
FIG. 1 is a side view of a stereotactic needle biopsy apparatus that may be used with the present invention for performing stereotactic mammographic guided surgical techniques on a breast using a rotary cutting surgical instrument.

FIG. 1 illustrates a prone stereotactic mammography biopsy apparatus which is typically used for stereotactic mammographic guided needle biopsies of the breast. A detailed description of the prone stereotactic apparatus 100 can be found in U.S. Pat. No. 5,289,520, which is incorporated herein by reference.

FIG. 2 illustrates a hand held rotary cutting surgical instrument made by U.S. Surgical Corporation and is referred to as the Surgi-Core. The instrument 10 basically comprises a body 12, a cannula 14 attached to the body 12, and a retractable, cylindrical, rotatable cutting or coring tip 16 disposed within the cannula 16. The instrument 10 further includes a window 18 from which a spur gear 20 protrudes. The spur gear 20 is connected to the cylindrical cutting tip 16 to provide a means for rotating the rotatable cutting tip 16. Ordinarily, the instrument 10 is used by hand and is equipped with a rack (not shown) which is attached to the body 12 at clips 22 and 24. The rack engages with spur gear 20 so that when the rack is moved back and forth in a reciprocating manner, the spur gear 50 is driven back and forth to cause reciprocating rotational movement of the cutting tip 16.

Figure 6:
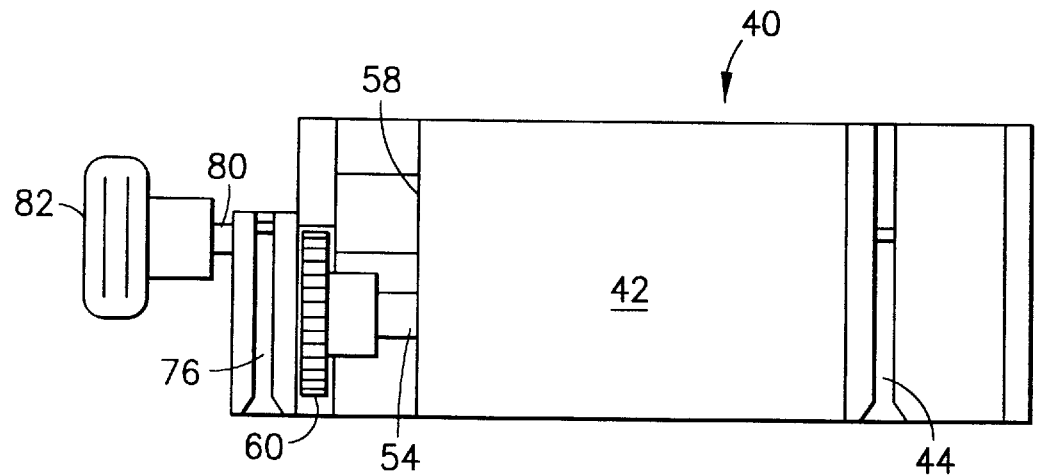
FIG. 6 is a top view of the apparatus of the present invention.
Figure 7:
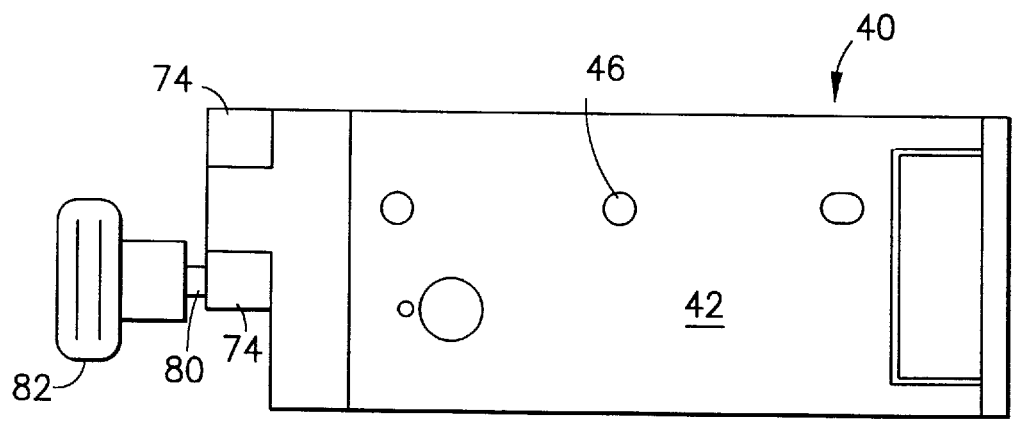
FIG. 7 is a bottom view of the apparatus of the present invention.

Referring to, FIGS. 3, 6 and 7, there is shown an apparatus 40 for attaching the hand held, surgical cutting instrument to a needle guiding stage of a stereotactic mammography apparatus. As will be explained below, the apparatus 40 is also able to drive the cutting tip of the instrument.

The apparatus 40 has a housing 42. A slot 44 is provided on a top side of the housing 42 and is sized to receive clip 24 of the surgical instrument 10. A threaded aperture 46 is provided on a bottom side of the housing 42 and is sized to receive a clamping bolt 118 of a standard needle holder 120 (FIG. 9) of needle guiding stage 122 on the stereotactic mammography needle biopsy apparatus 100 such as that shown in FIG. 1.

Figure 8:
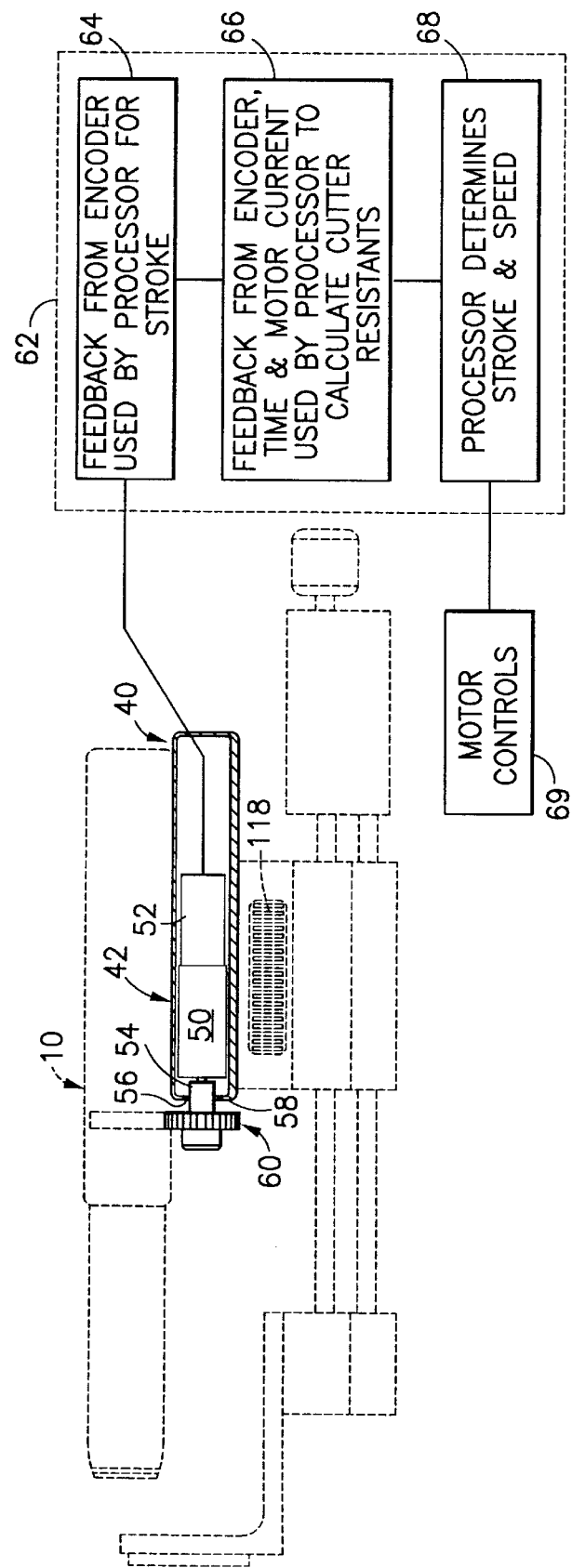
FIG. 8 is a cross-sectional view of the apparatus of the present invention illustrating the positioning of the motor and position encoder within the housing.
Figure 10:
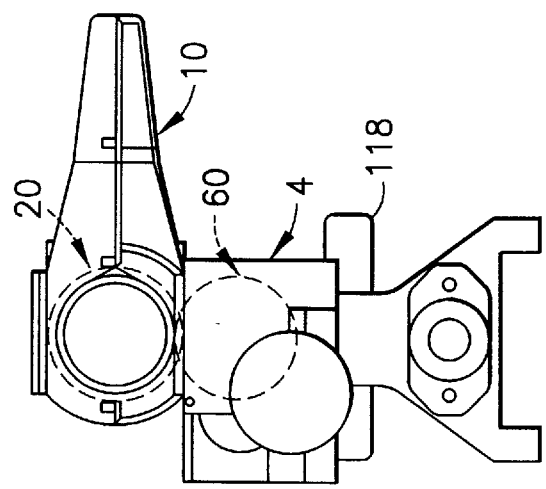

Referring to FIG. 8, a motor 50, having a shaft (not shown), is disposed within the housing 42. A position encoder 52 is also positioned within the housing 42 and is connected to the shaft of the motor 50. A drive shaft 54, having an end connected to the motor 50 shaft, extends through a shaft seal 56 positioned in an opening at drive end 58 of housing 42. A disposable gear 60 is fitted to the drive shaft 54 to engage spur gears 60 and 20 as shown in FIG. 10. Gear 60 is disposable to provide for a sterile environment.

The position encoder 52 is connected to a controller 62 which monitors the angular position of the motor 50. The controller 62 also monitors the electrical current drawn by the motor 50. As illustrated in flow diagram steps 64 through 68, based upon the angular velocity of the motor 50 as indicated by the position encoder 52 over a period of time and based upon the current drawn by the motor as monitored by the controller 62, the controller 62 calculates cutter resistance and can make appropriate adjustments to the angular velocity of the motor 50 via motor controls 69 to ensure that the cutting tip 16 is moving with the proper angular velocity.

In addition to controlling the proper angular velocity, controller 62 is also used to control the cutting stroke of the cutting tip 16 by monitoring the absolute angular position of the motor 50 via position encoder. When an angular limit is reached, the controller 62 reverses the motor's angular direction. Cutting stroke is defined as the angular displacement of the cutting tip in one direction, such as clockwise. Ordinarily, when the surgical instrument 10 is used by hand, the cutting tip 16 is rotated in a reciprocating manner, such as up to a 360° stroke in a clockwise direction and then a 360° stroke in a counter clockwise direction. The controller 62 offers an advantage over the hand control in that it can be programmed to provide any size and series of strokes desired in either of the two angular directions. For example, the controller 62 may be programmed to provide a 180° stroke in the clockwise direction and a 90° stroke in the counter clockwise direction.

Referring back to FIGS. 3, 4, 5 and 6, in the preferred embodiment, the apparatus 40 also includes a swing arm extension 70 which is attached to the drive end 58 of the housing 42. A swing arm 72 is pivotally mounted to the swing arm extension 70 at its pivot end 74. A slot 76 is provided on a free end 78 of the swing arm 72. The slot 76 is sized to receive clip 22 of the surgical instrument 10. A biasing bolt 80 with knob 82 is provided on the swing arm 72 to make fine adjustments to the distance between slot 76 on the swing arm 72 and slot 44 on the housing 42 of the apparatus 40 when the swing arm is placed in the vertical position (FIG. 3).

Referring to FIGS. 3, 4, 9 and 10, the surgical instrument 10 is held to the apparatus 40 by sliding clips 22 and 24 in slots 76 (swing arm in vertical position) and 44 respectively. By turning knob 82, which forces bolt 80 against the drive end 58 of the housing 42, movement of the surgical instrument 10 along the slots 44 and 72 is prevented because the distance of slot 76 on the swing arm 72 to slot 44 on the housing 42 is made slightly larger causing sufficient friction to prevent movement of the instrument 10. Spur gear 20 of the surgical instrument is driven by spur gear 50 of the apparatus 40.

As with any surgical procedure, sterile conditions are essential. When the surgical instrument 10 is removed from the apparatus 40, swing arm 72 may be pivoted as shown in FIG. 4 to allow removal and replacement of disposable gear 60.

It will thus be seen that the objects and advantages set forth above and those made apparent from the preceding descriptions, are efficiently attained and, since certain changes may be made in the above construction without departing from the scope of the invention, it is intended that the matter contained in the above description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. An apparatus for holding a rotary cutting surgical instrument to a needle guiding stage of a stereotactic mammography biopsy system and for driving the rotary cutting surgical instrument, the apparatus comprising:

a housing having means for holding the rotary cutting surgical instrument to the housing and having means for securing the housing to a needle guiding stage of a stereotactic mammography apparatus;

a rotation means for rotating the rotary cutting surgical instrument; and controlling means, connected to the rotation means, for determining a cutting resistance experienced by the rotary cutting surgical instrument and for controlling the rotation means in response to the cutting resistance.

2. An apparatus for holding a rotary cutting surgical instrument to a needle guiding stage of a stereotactic mammography biopsy system and for driving the rotary cutting surgical instrument, the apparatus comprising:

a housing having a holding means for holding the rotary cutting surgical instrument to the housing, having a means for securing the housing to a needle guiding stage of a stereotactic mammography apparatus, and having a drive end;

a motor having a shaft, the motor positioned within the housing;

a position encoder positioned within the housing, the position encoder connected to the shaft of the motor;

removable holding means, attached to the housing at the drive end, for holding the rotary cutting surgical instrument to the housing; and a transmission means for transmitting the rotational energy of the motor to the surgical cutting instrument, the transmission means connected to the shaft of the motor, the transmission means being located between the drive end of the housing and the removable holding means; and controlling means, connected to the motor, for determining a cutting resistance experienced by the rotary cutting surgical instrument and for controlling the motor in response to the cutting resistance.

3. An apparatus for holding a rotary cutting surgical instrument to a needle guiding stage of a stereotactic mammography biopsy system and for driving a rotary cutting surgical instrument, the apparatus comprising:

a housing having a first holding means for holding the rotary cutting surgical instrument to the housing, having a means for securing the housing to a needle guiding stage of a stereotactic mammography apparatus and having a drive end;

a motor having a shaft, the motor positioned within the housing;

a position encoder within the housing, the position encoder connected to the shaft of the motor;

a swing arm hingeably attached to the housing at the drive end, the swing arm having a holding means for holding the rotary cutting surgical instrument to the apparatus, the swing arm further including biasing means for adjusting the position of the holding means thereon relative to the holding means on the housing;

a gear connected to the shaft of the motor, the gear being located between a drive end of the housing and the swing arm; and controlling means, connected to the motor, for determining a cutting resistance experienced by the rotary cutting surgical instrument and for controlling the motor in response to the cutting resistance.

\* \* \* \* \*

UNITED STATES PATENT AND TRADEMARK OFFICE
CERTIFICATE OF CORRECTION

PATENT NO. : 5,830,219
DATED : November 3, 1998
INVENTOR(S) : Bird et al.

It is certified that error appears in the above-identified patent and that said Letters Patent is hereby corrected as shown below:

In the abstract, line 7: delete "a mechanism" and insert therefor --means--.

Figure 9:
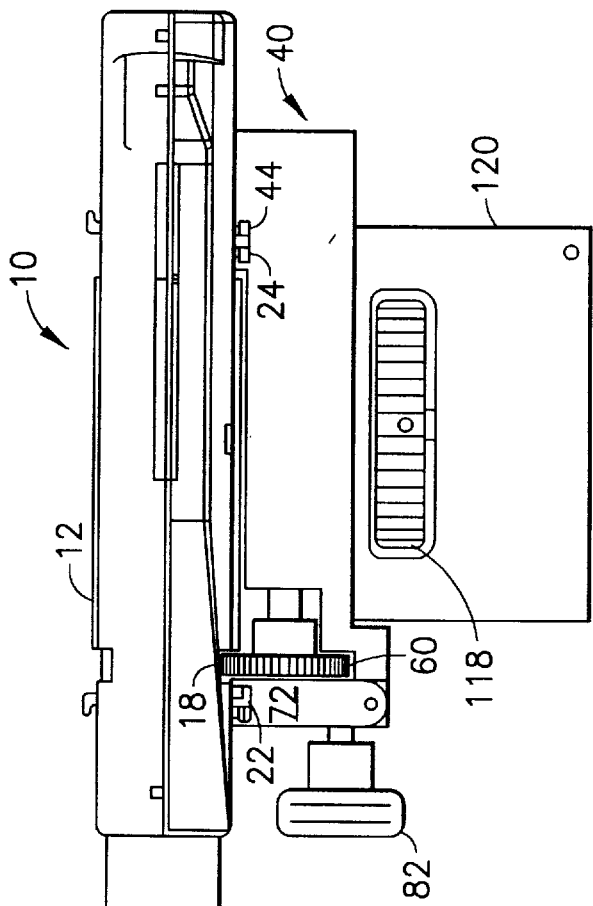
FIG. 9 is a side view of the apparatus having securely mounted thereon the rotary cutting surgical instrument, and wherein the apparatus is securely attached to the biopsy needle guiding stage of a stereotactic mammography apparatus.

In column 2, line 48: delete "FIG. 9 is a side view" and insert therefor --FIGS. 9 and 10 are side and end views--.

In column 3, line 12: after the word "to" delete ",".

In column 5, line 19: after the word "apparatus" insert --,--.

Signed and Sealed this

Fourth Day of May, 1999

Attest:

Q. TODD DICKINSON

*Attesting Officer*     *Acting Commissioner of Patents and Trademarks*